United States Patent
Ambriovic Ristov et al.

(10) Patent No.: US 12,360,112 B2
(45) Date of Patent: Jul. 15, 2025

(54) METHOD FOR IDENTIFICATION OF VIRUSES AND DIAGNOSTIC KIT USING THE SAME

(71) Applicant: RUDJER BOSKOVIC INSTITUTE, Zagreb (HR)

(72) Inventors: Andreja Ambriovic Ristov, Zagreb (HR); Dragomira Majhen, Zagreb (HR); Alen Kovacevic, Zagreb (HR)

(73) Assignee: RUDJER BOSKOVIC INSTITUTE, Zagreb (HR)

(*) Notice: Subject to any disclaimer, the term of this patent is extended or adjusted under 35 U.S.C. 154(b) by 330 days.

(21) Appl. No.: 17/413,902

(22) PCT Filed: Dec. 19, 2018

(86) PCT No.: PCT/HR2018/000023
§ 371 (c)(1),
(2) Date: Jun. 14, 2021

(87) PCT Pub. No.: WO2020/128538
PCT Pub. Date: Jun. 25, 2020

(65) Prior Publication Data
US 2024/0011989 A1  Jan. 11, 2024

(51) Int. Cl.
*G01N 33/569* (2006.01)
*G01N 1/40* (2006.01)
*G01N 33/543* (2006.01)
*G01N 33/68* (2006.01)

(52) U.S. Cl.
CPC .......... *G01N 33/56983* (2013.01); *G01N 1/40* (2013.01); *G01N 33/54326* (2013.01); *G01N 33/6848* (2013.01)

(58) Field of Classification Search
CPC ....... G01N 33/56983; G01N 33/54326; G01N 33/6848
See application file for complete search history.

(56) References Cited

U.S. PATENT DOCUMENTS

| | | | | |
|---|---|---|---|---|
| 5,538,897 | A | * | 7/1996 | Yates, III ........... G01N 33/6848 530/335 |
| 2003/0044771 | A1 | | 3/2003 | Anderson |
| 2010/0047767 | A1 | * | 2/2010 | Dehal ................. G01N 33/576 435/5 |

OTHER PUBLICATIONS

Yao ZP, Demirev PA, Fenselau C. Mass spectrometry-based proteolytic mapping for rapid virus identification. Anal Chem. Jun. 1, 2002;74(11):2529-34. (Year: 2002).*
Chou TC, Hsu W, Wang CH, Chen YJ, Fang JM. Rapid and specific influenza virus detection by functionalized magnetic nanoparticles and mass spectrometry. J Nanobiotechnology. Nov. 16, 2011;9:52. (Year: 2011).*
Singhal N, Kumar M, Kanaujia PK, Virdi JS. MALDI-TOF mass spectrometry: an emerging technology for microbial identification and diagnosis. Front Microbiol. Aug. 5, 2015;6:791. (Year: 2015).*
International Search Report mailed on Mar. 2, 2020 for WO 2020/128538 A1 (3 pages).
Zhong-Ping Yao et al., "Mass Spectrometry-Based Proteolytic Mapping for Rapid Virus Identification," Anal. Chem. 2002, 74, 11, 2529-2534, Apr. 30, 2002; Abstract only (1 page).
Sandra Pinkert et al., "The Coxsackievirus and Adenovirus Receptor: Glycosylation and the Extracellular D2 Domain Are Not Required for Coxsackievirus B3 Infection," J Virol May 2, 20167;90(12):5601-5610 (18 pages).

* cited by examiner

*Primary Examiner* — Janet L Andres
*Assistant Examiner* — Ruixue Wang
(74) *Attorney, Agent, or Firm* — Allan A. Fanucci

(57) ABSTRACT

This invention describes a novel method for identification of known and unknown viruses from various biological and non biological samples using carrier suitable for immobilisation of membrane proteins of different target cells of human, animal or bacterial origin for capturing the virus, whose peptides are identified by mass spectrometry analysis, a diagnostic kit based on the said method and the use thereof.

10 Claims, 6 Drawing Sheets
Specification includes a Sequence Listing.

Figure 4 a and Figure 4 b (c)

SEQUENCE LISTING

<160> NUMBER OF SEQ ID NOS: 7

<210> SEQ ID NO 1
<211> LENGTH: 17
<212> TYPE: PRT
<213> ORGANISM: Human adenovirus type 5
<220> FEATURE:
<221> NAME/KEY: misc_feature
<223> OTHER INFORMATION: Pre-histone like nucleoprotein; core protein
      precursor pVII [Human mastadenovirus C]

<400> SEQUENCE: 1

Arg Thr Thr Val Asp Asp Ala Ile Asp Ala Val Val Glu Glu Ala Arg
1               5                   10                  15

Asn

<210> SEQ ID NO 2
<211> LENGTH: 21
<212> TYPE: PRT
<213> ORGANISM: Human adenovirus type 5
<220> FEATURE:
<221> NAME/KEY: misc_feature
<223> OTHER INFORMATION: Hexon-interlacing protein; hexon associated
      protein [Human mastadenovirus C]

```
<400> SEQUENCE: 2

Arg Gly Ile Val Thr Asp Phe Ala Phe Leu Ser Pro Leu Ala Ser Ser
1               5                   10                  15

Ala Ala Ser Arg Ser
            20

<210> SEQ ID NO 3
<211> LENGTH: 9
<212> TYPE: PRT
<213> ORGANISM: Human adenovirus type 5
<220> FEATURE:
<221> NAME/KEY: misc_feature
<223> OTHER INFORMATION: Pre-histone like nucleoprotein; core protein
      precursor pVII [Human mastadenovirus C]

<400> SEQUENCE: 3

Arg Ala Pro Trp Gly Ala His Lys Arg
1               5

<210> SEQ ID NO 4
<211> LENGTH: 23
<212> TYPE: PRT
<213> ORGANISM: Human adenovirus type 5
<220> FEATURE:
<221> NAME/KEY: misc_feature
<223> OTHER INFORMATION: Pre-histone like nucleoprotein; core protein
      precursor pVII [Human mastadenovirus C]

<400> SEQUENCE: 4

Arg Asn Tyr Thr Pro Thr Pro Pro Val Ser Thr Val Asp Ala Ala
1               5                   10                  15

Ile Gln Thr Val Val Arg Gly
            20

<210> SEQ ID NO 5
<211> LENGTH: 12
<212> TYPE: PRT
<213> ORGANISM: Human adenovirus type 5
<220> FEATURE:
<221> NAME/KEY: misc_feature
<223> OTHER INFORMATION: pre-hexon-linking protein IIIa; capsid protein
      precursor pIIIa [Human mastadenovirus C]

<400> SEQUENCE: 5

Val Leu Ala Ile Val Asn Ala Leu Ala Glu Asn Arg
1               5                   10

<210> SEQ ID NO 6
<211> LENGTH: 12
<212> TYPE: PRT
<213> ORGANISM: Human adenovirus type 5
<220> FEATURE:
<221> NAME/KEY: misc_feature
<223> OTHER INFORMATION: pre-hexon-linking protein IIIa; capsid protein
      precursor pIIIa [Human mastadenovirus C]

<400> SEQUENCE: 6

Leu Ser Ala Ile Leu Glu Ala Val Val Pro Ala Arg
1               5                   10

<210> SEQ ID NO 7
<211> LENGTH: 17
<212> TYPE: PRT
<213> ORGANISM: Human adenovirus type 5
<220> FEATURE:
<221> NAME/KEY: misc_feature
```

```
<223> OTHER INFORMATION: pre-hexon-linking protein IIIa; capsid protein
      precursor pIIIa [Human mastadenovirus C]

<400> SEQUENCE: 7

Leu Leu Leu Leu Leu Leu Ala Pro Phe Thr Asp Ser Gly Ser Val Ser
1               5                   10                  15
Arg
```

METHOD FOR IDENTIFICATION OF VIRUSES AND DIAGNOSTIC KIT USING THE SAME

CROSS REFERENCE TO RELATED APPLICATIONS

This application is a national phase of PCT application No. PCT/HR2018/000023, filed on 19 Dec. 2018, of which is incorporated herein by reference.

REFERENCE TO SEQUENCE LISTING SUBMITTED VIA EFS-WEB

This application includes an electronically submitted sequence listing in PDF format. The PDF file contains a sequence listing entitled "885-1109_SEQ_ST25.pdf" created on Nov. 16, 2022, and is 58.1 KB (59,562 bytes) in size. The sequence listing contained in this PDF file is part of the specification and is hereby incorporated by reference herein in its entirety.

FIELD OF THE INVENTION

This invention is related to the novel method for identification of viruses from a sample derived from various biological and non-biological origin. This method is a multistep procedure using carrier suitable for immobilisation of proteins coupled to the membrane proteins of different target cells of human, animal or bacterial origin for capturing the virus, elution of virus, digestion into peptides, and further identifying it by mass spectrometry (MS) analysis. Method can be used in various fields of clinical virology, food analysis, monitoring and control of biotechnological processes, monitoring of rivers, lakes, sea water, water works, ventilation system, soil, objects from the animal and human living space and the like. Basic principle of the method allows for the first time to isolate and identify known and unknown viruses without any culturing step, in a very fast and reliable way and without any previous knowledge of the virus type present in the sample.

BACKGROUND OF THE INVENTION

The identification of pathogen viruses is of critical importance to clinical microbiology, infectious diseases and public health in general. This is especially true in cases of threats of bioterrorism in which biological agents (most prominently viruses) are used or threatened to be used in order to cause disease or death among human population or food crops and livestock, new emerging viral diseases which are rapidly expanding due to the global migrations of people, re-emerging of eradicated diseases and novel emerging pathogen viruses. Additionally, many industrial processes such as food processing and biotechnological process production need to be monitored in terms of viral contamination, among other things.

This is often not easy since currently available methods are either not applicable for unknown viruses (RNA/DNA analysis methods), time consuming, not sensitive enough, expensive or not reliable.

Traditional methods used for the identification of known and unknown viruses include: electron microscopy (virus visualisation) and cultivation in cell culture. These methods have serious drawbacks since they are time-consuming, often not sensitive enough, require substantial technical skills and are not able to provide reliable and reproducible results. These methods are currently replaced by methods which allowed screening and more reliable diagnostics of viral infections. Some of these methods use specific anti-viral antibodies which include: immunofluorescent assay, numerous variants of enzyme-linked immunoassay (EIA) including enzyme-linked immunosorbent (ELISA) and Western blot assay, for example. These methods are widely used now but also have limitations which are inconsistencies in the testing, high risk of interferences, high cost and most importantly a priori knowledge of potential pathogens is needed (Chiu, C Y, Viral pathogen discovery, Current Opinion in Microbiology 2013, 16:468-478; Boonham N, et al. Methods in Virus diagnostics: from ELISA to Next Generation Sequencing, Virus Research, 2014, 186: 20-31, doi: 10.1016/j.virusres.2013.12.007; Seouf S, Recent Advances in Diagnostic Testing for Viral Infections, BioscienceHorizons, 2016, 9:1-11, doi: 10.1093/biohorizons/hzw010).

Genomic approach for identification of virus pathogen include polymerase chain reaction (PCR) and modification thereof (NAAT, nucleic acid amplification test). PCR method is one of the most widely used laboratory method for detection of viral nucleic acids nowadays. This method is highly sensitive, highly specific but requires specific primers for the target which means that a priori knowledge of the potential viral pathogen is necessary and excludes the possibility of discovery of and characterisation of unknown viruses.

Next generation sequencing (NGS) or deep sequencing is one of the new approaches in virus diagnostics. This approach involves analysis of millions of sequences derived from nucleic acid present in the sample and enables the analysis without a priori knowledge of the virus present in the sample. The main drawbacks of this method are high costs, needs for bioinformatics skills for data analysis and huge workload. Therefore such method cannot be used for large number of analyses and is not applicable to routine clinical diagnostics (Seouf S, Recent Advances in Diagnostic Testing for Viral Infections, BioscienceHorizons, 2016, 9:1-11, doi: 10.1093/biohorizons/hzw010).

Additionally, pan-viral microarrays approach is currently available. Pan-viral microarrays attempt to represent all known viruses using tens of thousands of oligonucleotide probes. Known viruses can be detected on the microarray, as well as novel viruses with at least some degree of relatedness to known viruses. It is a high cost method having limitations for clinical use due to the complexity of assay. Moreover, viruses from yet undiscovered families will not be detected by this approach.

MS spectrometry has been used in the viral research (p.e. WO9525281 A1, Identification of Nucleotides, Amino Acids or Carbohydrates by Mass Spectrometry; WO 2011/067516 A1, Method for Quick Identification of Viruses by Means of Spectroscopy; US 2011/0130311, Method and System for Diagnosing Virus) so far. Method relies on lysing virus present in the sample, treating the lysed sample with a specific protease to digest a protein in the sample into peptides and converting the sample into charged particles (ions) by ionisation process. These ions are separated according to their mass to charge ratio and analysed by a detector. The result obtained is compared to a reference database and delivered as an interpretative spectrum. However, this method has limitations and one of the most important is incapability of the method of discovery of unknown viruses.

Therefore, technical problem to be solved by this invention is to provide rapid and reliable method for diagnosis (identification of virus pathogen) which does not require and a priori knowledge of the potential viral pathogens in the sample to be tested and which does not require cultivation of the virus prior analysis. This new method is needed in order to ensure timely therapy and prevent complications, collect epidemiological data and prevent outbreaks and spreading of the diseases and additionally to ensure monitoring of virus contamination in biotechnology, pharmaceutical, food industry and the like. The method should be fast, reliable and applicable to identification of known viruses as well as unknown viruses.

BRIEF DESCRIPTION OF THE INVENTION

This invention describes method for identification viruses in a sample comprising following steps: a) collecting and optionally concentrating the sample, b) isolation of membrane proteins of target cells; c) coupling of the membrane proteins isolated in step b) to a carrier suitable for immobilisation of proteins obtaining carrier with immobilised membrane proteins, d) incubating sample with preparation obtained in step c), e) separating carrier with immobilised membrane proteins having attached the virus particle, f) detaching the virus particle from the carrier with immobilised membrane proteins, g) preparation of the sample for the MS (mass spectrometry) analysis, h) determination of the viral peptide sequence/s obtained by step g), i) identification of the virus by comparing the structure/s identified in step g) with databases of virus peptide sequences (known virus) or, using sequences identified in step h) for identification of a new virus by the RNA/DNA analysis methods (unknown virus).

The invention is based on the fact that viruses enter the target cell by specifically attaching to the receptor exposed on the membrane of the target cell (Yamauchi Y, Helenius A: Virus entry at a glance, J Cell Sci 2013, 126: 1289-1295; doi: 10.1242/jcs.119685). This phenomenon is used to specifically attach the virus to a carrier suitable for immobilisation of proteins coupled to the membrane proteins of target cells (Olsvik O et al. Magnetic separation techniques in diagnostic microbiology. Clin Microbiol Rev. 1994 7(1):43-54, doi: 10.1128/CMR.7.1.43); the virus can subsequently be released and readily analysed by mass spectrometry. The results are then compared with databases of known virus peptide sequences and the virus in the sample is identified. In case of no match with any known virus from the said databases, this could mean that new virus have been discovered. In both cases—presence of known and unknown virus could be optionally further verified by detecting the viral genetic material (DNA or RNA) via standard PCR or RT-PCR, if needed. In this way both known and unknown viruses could be detected and identified without a priori knowledge of the potential pathogen in the sample to be tested.

BRIEF DESCRIPTION OF THE FIGURES

FIG. 2. Coxsackievirus and adenovirus receptor (CAR) expression for (a) RD, (b) RD-A7 and (c) RD-G7 cells. RD, RD-A7 and RD-G7 cells were detached by Versene and analysed by flow cytometry using murine monoclonal antibody anti-CAR, clone RmcB followed by rabbit PE-conjugated-antimouse antibody. Hystogram showing IgG1 isotype control is represented in black and hystogram showing anti-CAR (clone RmcB) is shown in grey.

DETAILED DESCRIPTION OF THE INVENTION

This invention relates to the method for identification of known and unknown viruses in a sample, which does not require a priori knowledge of potential pathogens. Method according to this invention comprises following steps:
  a) collecting and optionally concentrating the sample
  b) isolation of membrane proteins of target cells
  c) coupling of the membrane proteins isolated in step b) to a carrier suitable for immobilisation of proteins obtaining carrier with immobilised membrane proteins
  d) incubating sample with preparation obtained in step c)
  e) separating carrier with immobilised membrane proteins having attached the virus particle
  f) detaching the virus particle from the carrier with immobilised membrane proteins
  g) preparation of the sample for the MS (mass spectrometry) analysis
  h) determination of the viral peptide sequence/s obtained by step g)
  i) identification of the virus by comparing the structure/s identified in step h) with databases of known virus peptide sequences (known virus) or, using sequences identified in step h) for identification of a new virus by the RNA/DNA analysis methods (unknown virus).

In one embodiment of the invention sample to be tested is a biological sample derived from blood, body liquids such as liquor, saliva and the like and any tissue sample of a human or animal origin or any swab taken from human or animal subject.

In another embodiment of the current invention sample is non-biological sample, preferably environmental sample taken from river, lake, sea, water conduit, water works, ventilation system and like, sample taken from soil or swab taken from any object, preferably object present in the human or animal living space, industry process quality control where the said industry is food processing industry, pharmaceutical or biotechnology based industry.

The sample to be tested could be used directly in the form taken or optionally prepared for testing by concentrating used known methods (e.g. from water: Cashdollar J L and Wymer L.: Methods for primary concentration of viruses from water samples: a review and meta-analysis of recent studies. J Appl Microbiol., 115(1):1-11, 2013, doi: 10.1111/jam.12143).

Target cells are selected from the group comprising: primary cells, any immortalised or tumour cell lines from different origin in human or animal body; or any bacterial strain cells.

The term "primary cells" means that it is a population of cells from a multicellular organism that are taken directly from living tissue (e.g. biopsy material) and established for growth in vitro. These cells have undergone very few population doublings.

The term "immortalized cells" means that it is a population of cells from a multicellular organism due to mutation, escape normal cellular senescence and keep undergoing division. Thus, this kind of cells can grow in vitro for prolonged periods The term "cancer cells" means that this is a population of cells from a multicellular organism that divide relentlessly, forming solid tumors or flooding the blood with abnormal cells.

Isolation of membrane proteins of target cells are performed using method standard in the art (Smith S M, Strategies for the Purification of Membrane Proteins in Walls D and Loughran S T (eds.) Protein Chromatography, Methods and Protocols, Methods in Molecular Biology, 2011, 681:485-496, doi: 10.1007/978-1-60761-913-0_29, Springer Science+Business Media; Lai X, A Reproducible Method to enrich Membrane Proteins with High-purity and High-yield for an LC-MS/MS approach in quantitative membrane proteomics. Electrophoresis, 2013, 34(6):809-817, doi: 10.1002/elps.201200503). "Carrier suitable for immobilisation of proteins" according to this invention is described as any carrier suitable for immobilisation of proteins and it is preferably selected from the group comprising: magnetic beads, agarose beads and the like (Meldal M and Schoffelen S, Recent advances in covalent, site specific protein immobilization. F1000Research 2016, 5:2303; Zucca P et al. Agarose and Its Derivatives as Supports for Enzyme Immobilisation. Molecules 2016, 21:1577, doi: 10.3390/molecules21111577; Mohamad N R et al. An Overview of Technologies for Immobilisation of Enzymes and Surface Analysis Techniques for Immobilized Enzymes, Biotechnology & Biotechnological Equipment, 2015, 29(2), 205-220, doi: 10.1080/13102818.2015.1008192).

Therefore, the different embodiments of this invention could be achieved by changing the type of target cells and consequently the receptors on their surface, and further coupling of membrane proteins from different targets cells to carrier suitable for immobilisation of proteins which are consequently then capable to attach viruses having specificity for exact receptor exposed on the surface of the particular cell, wide variety of human, animal or bacterial viruses can be detected and identified.

Viruses are detached from the carrier with immobilised membrane proteins by method know in the art (Protein Purification Protocols, doi: 10.1385/159259655X) and prepared for the MS analysis according to standard methodology known in the art (Preparation of Proteins and Peptides for Mass Spectrometry Analysis in a Bottom-Up Proteomics Workflow, doi: 10.1002/0471142727.mb1025s88). Peptide sequences are then analysed and their structure compared to databases of known proteins (for example Swiss or Uniprot).

In one embodiment the method according to the invention is used for identification of known viruses in case of finding the peptide structure which resulted from MS analysis in the databases of known viruses. Presence of viral DNA or RNA can be verified by standard PCR or RT-PCR methodology (Ambriović Ristov A. et al. (Ed) (2007) Metode u molekularnoj biologiji, Institut Ruder Bošković, Zagreb, ISBN: 978-953-6690-72-5).

In yet another embodiment the method according to the invention is used for characterisation of unknown viruses. In this peptide structure which resulted from MS analysis could not be found in the databases of known viruses. In this case also Presence of viral DNA or RNA can be verified by standard PCR or RT-PCR methodology.

Present invention further encompasses carrier with immobilised membrane proteins of target cells for use in identification of known viruses or characterisation of unknown viruses.

Present invention further describes diagnostic kit comprising carrier with immobilised membrane proteins of target cells, leaflet containing instructions for use and optionally chemicals needed for carrying out steps e)-g) of the method according to the invention.

Target cells used for developing the diagnostic kit according to the invention could be selected from the group comprising: primary cells, any immortalised or tumour cell lines from different origin in human or animal body; or any bacterial strain cells.

By varying the target cells used for developing of the said diagnostic kit, different diagnostic sets could be developed which are capable for detecting for example human respiratory viruses wherein respiratory tract cells are used as target cells. Another example may include diagnostic kit based on liver cells for detection of liver pathogen viruses, cells from nervous system to detect viruses capable of infecting brain and spinal cord and cells from skin to detect viruses causing skin infection. These are only given as an example which does not in any case limit the spectrum of the target cells and therefore the diagnostic kit based on thereof.

Present invention also describes use of the diagnostic kit to detect the known and unknown virus in a sample to be tested which according to the invention could be a biological sample derived from blood, body liquids such as liquor, saliva and the like and any tissue sample of a human or animal origin or any swab taken from human or animal subject.

In another embodiment of the current invention sample is non-biological sample, preferably environmental sample taken from river, lake, sea, water conduit, water works, ventilation system and like, sample taken from soil or swab taken from any object, preferably object present in the human or animal housing, industry process quality control where the said industry is food processing industry, pharmaceutical or biotechnology based industry.

EXAMPLES

Experimental Model

As experimental model for demonstration of technical viability of this invention and obtaining experimental proofs of the concept in general, pathogen adenovirus type 5 (Ad5) was chosen together with two stably transfected cell clones of human rhabdomyosarcoma cells (RD-A7 and RD-G7) which express primary receptor for Ad5 at the cell surface, namely coxsackievirus and adenovirus receptor (CAR) (Nemerow et al., Virology. 2009 Feb. 20; 384(2):380-8, Majhen et al. Life Sci. 2011 Aug. 15; 89(7-8):241-9). Wild type RD cells have negative CAR phenotype and in the following experiments were used as negative control.

Methodology

1. Cultivation of RD, RD-A7 and RD-G7 cells

The human rhabdomyosarcoma (RD) cell line was obtained from the American Type Culture Collection (CCL-136, ATCC; USA). RD-A7 and RD-G7 cells were obtained as described in Majhen et al. Life Sci. 2011 Aug. 15; 89(7-8):241-9. Cells were grown in vitro in Petri dishes having diameter of 10 cm in the moisture saturated atmosphere at 37° C. with 5% $CO_2$. Dulbecco's modificated Eagle's cultivation medium with addition of 10% of fetal bovine serum (DMEM-FBS medium; Fetal Bovine Serum, Sigma F7524; Dulbecco's Modified Eagle's Medium—high glucose, Sigma D5796) was used for cultivation. After 3 days cells were inoculated in fresh medium in order to avoid dying because of the exhaustion of the cell growth medium.

2. Thawing, Sub-Culturing and Freezing of RD, RD-7 and RD-G7 Cells

Ampoules with frozen cell were taken out of the liquid nitrogen and incubated in water bath until completely defrosted. Cell were transferred to the Petri dishes having diameter of 10 cm containing 9 mL of the DMEM-FBS medium, warmed up previously to 37° C. in a water bath. Next day, after the check-up under light microscope, the growth medium has been replaced, and according to requirements, cells were sub-cultured.

When sub-culturing, DMEM-FBS was removed from Petri dishes and the cells were washed with previously warmed up trypsin, 0.25%, Trypsin-EDTA solution, Sigma T4049 37° C.). After washing, cells were incubated in 1 mL of fresh trypsin until they start to detach from the bottom. Trypsin action was blocked by adding 9 ml of the DMEM-FBS medium (previously warmed up to 37° C. in a water bath). Cell were then resuspended by multiple pipetting up and down and evenly distributed to new Petri dishes so as to have $1.5 \times 10^6$ cells per each.

For the purpose of freezing, cells were detached from the bottom with the trypsin solution as described above. After counting of cells, cell suspension was transferred to 15 ml plastic tube and centrifuged at 1100×g during 10 min. Cell pellet was resuspended in the 950 μL of the DMEM-FBS medium, and cryopreservation agent DMSO at final concentration of 5% was added to the cell suspension. Ampoules for freezing were kept on ice during 30 minutes and then added to the rack of the liquid nitrogen container (−80° C.).

3. *Mycoplasma* Test

RD, RD-7 and RD-G7 cells ($5 \times 10^3$ cell per each cell line) were grown on microscope slides using DMEM-FBS growth medium without antibiotics. Five days from inoculation, cells were fixed with acetic acid:methanol (3:1) and incubated with Hoechst 33258 dye (50 ng/mL in PBS) in dark at room temperature for 10 min. Cells were washed with $deH_2O$, and mounted using mounting solution (22.2 mM citric acid and 55.6 mM $Na_2HPO_4$ in 50% glycerol, pH 5.5) and inspected by fluorescent microscope.

4. Assessing Expression of CAR in the Cell RD, RD-A7 and RD-G7 Using Flow Cytometry Method RD, RD-A7 and RD-G7 cells were trypsinized and centrifuged 10 min at 1100×g and at room temperature and the medium in supernatant was discarded. Cell pellet was washed for the first time with 5 mL and second time with 8 mL of PBS which did not contain Ca++ and Mg++. Cell were centrifuged again for 10 min at 1100×g and at room temperature and resuspended in 10 mL of cold PBS without Ca++ and Mg++. From each sample, $5 \times 10^5$ cell/50 μl were transferred to the flow cytometry tubes. Cells were incubated with primary antibody murine mAb anti-CAR, clone RmcB (Upstate Cell Signaling Solutions, USA) for 1 h on ice with occasional shaking of the tubes in order for antibody to be evenly distributed. After incubation, samples were washed 2 times with 450 μL of PBS without Ca++ and Mg++ and secondary antibody FITC Goat Anti-Mouse IgG Clone Polyclonal (RUO), BD Bioscience, was added. Incubation with secondary antibody lasted 30 min on ice with occasional gentle shaking of tubes in order for antibody to be evenly distributed. Cells were washed for three times with 450 μL cold PBS without Mg and Ca, and pellet was finally dissolved in 400 μL of 0.1% BSA in PBS without Ca++ and Mg++, after which expression of CAR was measured using flow cytometer. Antibodies used in the experiment are shown in Table 1.

TABLE 1

Final concentration and volume of primary and secondary antibodies used in measurement of CAR expression by flow cytometry method.

| | ANTIBODY | CONCENTRATION/μg/mL | VOLUME/ μL |
|---|---|---|---|
| Primary Antibodies | IgG1 isotype control | 3.63 | 1.0 |
| | RmcB, anti-CAR | 14.54 | 0.8 |
| Secondary Antibodies | Goat antibodies against mouse immunoglobulins | 9.09 | 1.0 |

5. Isolation of Membrane Proteins from RD, RD-A7 and RD-G7 Cell Lines 5.1. Abcam Plasma Protein Extraction Kit (ab65400)

Cell lines were grown using methodology described in the above section 1 until minimum of $5 \times 10^8$ cells was reached per each cell line. On the cell collection day for the purpose of isolation of plasma membrane proteins, one of the Petri dish of each cell line was used for counting the cells. The total number of cell of the same clone was obtained by multiplying of the cell number in one Petri dish with the number of Petri dishes of the same clone.

Cells were collected by scratching in cold PBS and then centrifuged for 10 min at 1100×g. Pellet was washed with 3 mL of cold PBS and resuspended in 2 mL of homogenisation buffer in cold Dounce homogenizer. Cells were homogenised on ice 50 times. Plasma membrane proteins from RD, RD-A7 and RD-G7 cell lines were isolated by making use of Abcam Plasma Protein Extraction Kit (ab65400) using the manufacturer's instructions and kept at −80° C. in PBS with 0.5% Triton X-100.

5.2. Isolation of Membrane Proteins Using Ultracentrifugation

Dry pellets of RD, RD-A7 and RD-G7 cells (~$10^8$ cells from each cell line) were washed with 3 mL of PBS without Ca++ and Mg++ by centrifuging at 1100×g, 10 min. Pellets were then resuspended in 2 mL of homogenization buffer from Abcam Plasma Protein Extraction Kit (ab65400) with addition of protease inhibitor according to manufacturer's instructions and homogenized in previously cooled Dounce homogenizer with larger pestle (Dounce tissue grinder set, Sigma D8938; pestle A clearance 0.0030-0.0050 in., pestle B clearance 0.0005-0.0025 in., working volume×L 2 mL×60 mm) 100 times. In order to remove cells that were not broken down together with nuclei, homogenates were centrifuged at 1000×g, 5 min at 4° C. Supernatants were transferred to ultracentrifuge cuvettes and centrifuged at 15000×g, 20 min at 4° C. In this step mitochondria and larger cell elements are pelleted and supernatants were transferred into new ultracentrifuge cuvettes and centrifuged at 100000×g at 4° C. during 1 h. Supernatants were discarded and the pellets containing membrane proteins were dissolved in 100 µl PBS without Ca++ and Mg++ with 0.5% Triton X-100. Samples were then sonicated 3 times for 3 seconds, aliquoted and kept at −80° C.

6. Determination of the Concentration of Total Isolated Membrane Proteins with BCA Method Concentrations of total isolated membrane proteins from cell lines RD, RD-A7 and RD-G7 were determined by making use of Pierce$^{TC}$ BCA Protein Assay Kit according to manufacturer's instructions. All samples were diluted 10× and transferred to the plate in duplicates. Absorbance was measured at wavelength 570 nm.

Calibration curve was made using standard BSA concentrations (125, 250, 500, 1000 and 1500 µg/mL) and concentration of proteins to be measured were calculated using formula: c (µg/mL)=(Abs−b) (100*a), where c is protein concentration, Abs final absorbance, b is ordinate segment and a plunge of the axis.

7. Western Blot Analysis of CAR in Isolated Membrane Proteins

Samples of isolated membrane proteins of RD, RD-A7 and RD-G7 cell lines were incubated in non-reducing buffer (Tris 1M pH 6.8, SDS 10%, glycerol 4 mL, Brophenol Blue 20 mg, mqH$_2$O 5 mL) during 10 min at 37° C. and then loaded on 12% sodium dodecyl sulfate polyacrylamide gel, 30 µg per well. Proteins were subjected to electric current with constant voltage of 80 V during 30 min, 100 V during 1.5 h. Upon electrophoresis, samples were transferred to nitrocellulose membrane under constant current of 400 A during 90 min. The membrane was washed in TBST (Tris buffered saline with Tween-20: 100 mM TrisHCl, 1.5M NaCl, 0.5% Tween-20, pH 7.5) and blocked using PBS with 5% nonfat dry milk and 0.1% Tween-20 in order to prevent nonspecific bonding of the primary antibody. After that membrane was incubated with primary antibody anti-CAR (RmcB clone) which was diluted 1:1000 in TBST with 5% nonfat dry milk overnight at 4° C. Next day, membrane was washed again with TBST and incubated with secondary antibody against mouse immunoglobulins diluted 1:5000 in TBST with 5% nonfat dry milk on a shaker during 2 h at room temperature. Membrane was washed with TBST and incubated with a chemiluminescence reagent during 1 min, exposed to X-ray film which was developed in the dark room.

8. Coupling Membrane Proteins on Dynabeads M-280 and Incubation of Conjugated Magnetic Particle with Adenovirus Type 5

Membrane proteins isolated from RD, RD-A7 and RD-G7 cell lines were conjugated with Dynabeads® M-280 Tosylactivated according to manufacturer's instructions using magnets DynaMag™-2. Incubation of magnetic particles with membrane proteins took place on rotor overnight at 5 rpm and at 4° C. Mass of the incubated magnetic particles and membrane proteins are shown in Table 2.

TABLE 2

Conditions for coupling of magnetic particles with membrane proteins

| Cell lines from which membrane proteins were isolated | Mass (volume) of magnetic particles | Mass (volume) of membrane proteins |
|---|---|---|
| RD | 5.00 mg (165.00 µL) | 100 µg (11.25 µL) |
| RD-A7 | 5.00 mg (165.00 µL) | 64.97 µg (10.10 µL) |
| RD-G7 | 5.00 mg (165.00 µL) | 100 µg (7.97 µL) |

Magnetic particles with immobilised membrane proteins were incubated with 10 µL of Adenovirus type 5 (Ad5) (Majhen et al., Biochem Biophys Res Commun. 2006 Sep. 15; 348(1):278-87.) having concentration of $7.14 \times 10^{11}$ pp/mL overnight at 5 rpm at 4° C. Magnetic particles were then washed with 0.1% BSA in PBS, pH 7.4, in order to remove non-bound and non-specifically bound Ad5 particles. Elution of the linked Ad5 particles from conjugated magnetic particles was performed by changing of ionic strength with 0.845 M NaCl (100 µL) on a shaker during 30 min at 700 rpm and at room temperature.

Eluates of Ad5 from conjugated magnetic beads were used final analysis using mass spectrometry.

9. LC-MS Non Targeted Mass Spectrometry Analysis

Analysis was done using following instruments and software: Autoflex Speed MALDI TOF/TOF, Bruker, Germany; Dionex Ultimate 3000 RSLCnano System, Thermo Scientific, SAD; Proteineer fcII, Bruker, Germany; FlexControl 3.4, Bruker, Germany; ProteinScape 3.0, Bruker, Germany; Hystar 3.2, Bruker, Germany; WARP-LC 1.3, Bruker, Germany; Chromeleon Xpress 6.8, Thermo Scientific, SAD. Sample digestion was done by using Trypsin over 18 h at 37° C. with shaking. Peptide separation was done by Dionex Ultimate 3000 RSLC nano System with UV/VIS detector (Thermo Scientific, SAD). Belonging column for peptide purification and separation was used. Peptide fractions were collected and deposited onto MALDI plate by using Proteinees fcII, Bruker, Germany. Peptide analysis was performed by mass spectrometer Autoflex Speed MALDI TOF/TOF (Bruker, Germany). External spectral calibration was done by cubic enhanced algorithm using signals obtained by recording spectra from peptides of known masses. MS and MS/MS spectra identification was done by software ProteinScape 3.0, Bruker, Germany. For verifying identifying peptides from the virus sample human Ad5 (unreviewed) data base from www.uniprot.org was used.

10. LC-MS Targeted Mass Spectrometry Analysis

Analysis was done using following instruments and software: 6460 Triple Quad LC/MS Agilent technologies, SAD; 1290 Infinity LC System, Agilent Technology, SAD; chromatographic column Acquity UPLC BEH C18 1.7 µm, 2.1×150 mm, Waters, SAD; MassHunter Workstation software, LC/MS Data acquisition B.07.00, Agilent Technologies, SAD. Purified Ad5 samples used in this analysis were first desalted and then digested by using RapiGest SF Surfactant (Waters, SAD). RD and RD-G7 samples were prepared in same way as for non-targeted analysis. Peptide separation was done by 1290 Infinity LC System directly connected to 6460 Triple Quad LC/MS. MS spectra obtained for Ad5 was used as a reference for identification of peptides obtained in MS of RD and RD-G7 samples.

Results

1. *Mycoplasma* Test—Negative Result

Figure 1:
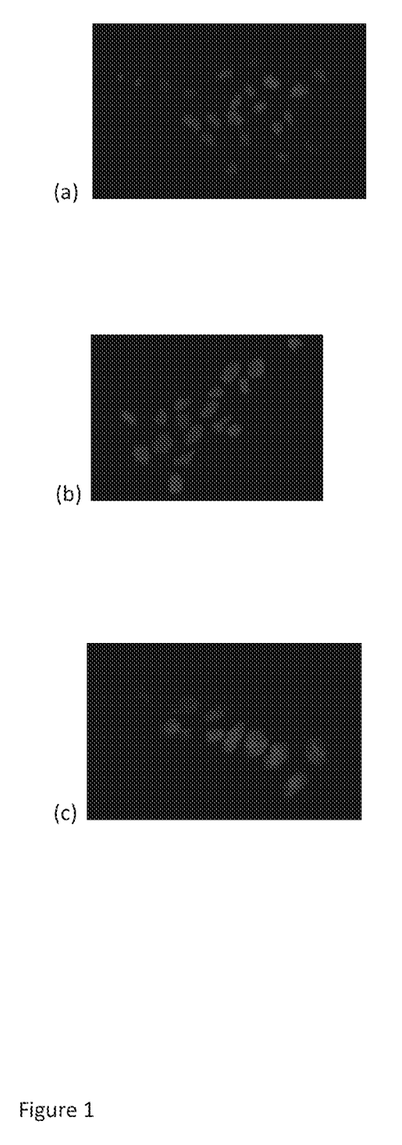
FIG. 1. Viable human rhabdomyosarcoma (RD) cell line obtained from the American Type Culture Collection (CCL-136, ATCC; USA) and RD cells stably transfected with a plasmid containing gene for coxsackievirus and adenovirus receptor (CAR) (plasmid pCDNA3-hCAR, Kim M et al. The coxsackievirus and adenovirus receptor acts as a tumour suppressor in malignant glioma cells, Br J Cancer, 2003, 88(9):1411-6, doi: 10.1038/sj.bjc.6600932): (a) RD, (b) RD-A7 and (c) RD-G7, dyed with Hoechst 33258 dye, imaging was performed by epifluorescence of 330/380 nm and LP 440 nm protective filter.

All three cell lines (RD, RD-A7 and RD-G7) were tested for presence of *mycoplasma* in order to confirm that samples were not contaminated by this frequent contaminant. FIG. 1 shows photographs of the RD, RD-A7 and RD-G7 cells viewed by fluorescent microscope. In case of positive test result, DNA intercalating dye Hoechst 33258 would be linked to the human as well as *mycoplasma* genom. Linking of Hoechst 33258 dye would be seen on the microscopic images as dotted colouring in the cytoplasm of the tested cells as well as intracellular compartments, which was not present in this case.

2. Confirmation of RD-A7 and RD-G7 Expression of CAR on their Surface

Figure 2:
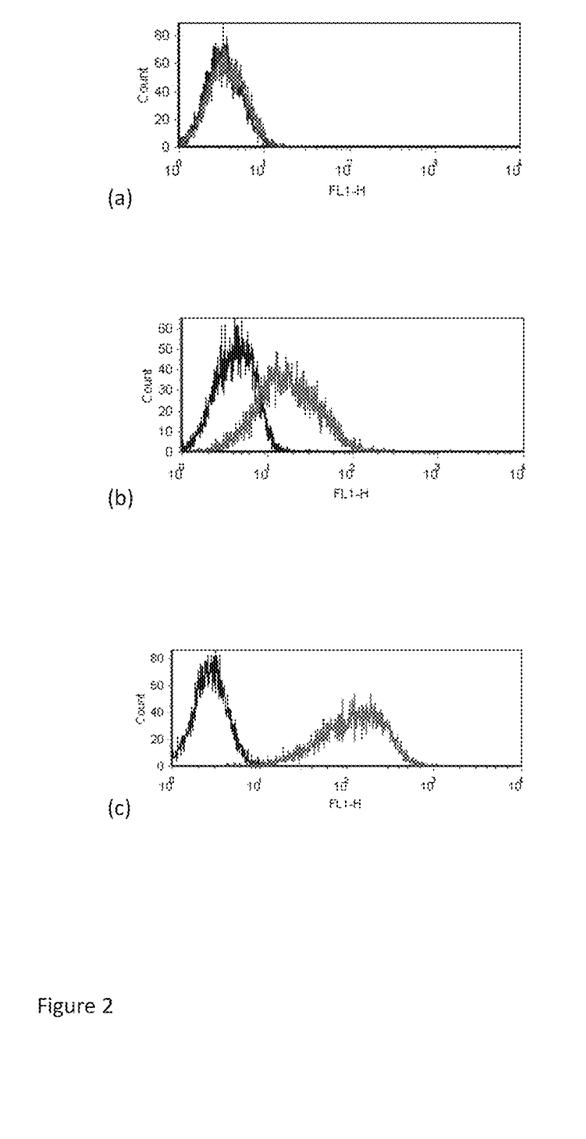

In order to check whether human adenovirus type 5 (Ad5) primary receptor (CAR) is present at the surface of RD, RD-A7 and RD-G7 cell lines, flow cytometry method using anti-CAR (RmcB) antibodies were performed. Results show (see FIG. 2) that CAR was not present in RD cells (a) while its presence was confirmed in stable transfectants RD-A7 (b) and RD-G7 (c). Comparison of histograms (b) and (c) revealed that CAR is expressed in greater amounts on the RD-G7 cell surface than on RD-A7 cell surface making them more susceptible to infection by Ad5.

3. Measurement of Concentration of Membrane Proteins Isolated from RD, RD-A7 and RD-G7 Cell Lines Table 3. shows concentrations of membrane proteins isolated from RD, RD-A7 and RD-G7 cell lines used in proteomic analysis described in the section 6 of Methodology part.

| \multicolumn{3}{c}{Concentrations of membrane proteins isolated from RD, RD-A7 and RD-G7, used in proteomic analysis.} | | |
|---|---|---|
| Sample | c (µg/µL) | m (µg) |
| RD | 8,882 | 1332,30 |
| RD-A7 | 9,817 | 1472,55 |
| RD-G7 | 12,542 | 1881,30 |

Figure 3:
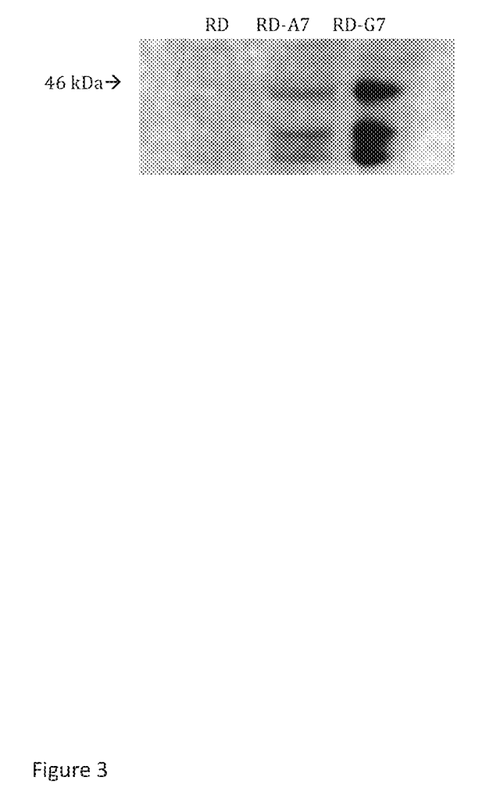
FIG. 3. Enriching primary receptor for Ad5 (46 kDa) in plasma membrane protein fraction isolated from cell lines RD-A7 and RD-G7 as compared to RD cells. Isolated membrane proteins were separated on 10% SDS-PAGE, transferred to a nitrocellulose membrane and Western blot analysis was performed using mouse monoclonal antibody anti-CAR (RmcB clone) diluted in ratio 1:10000 and secondary antibody against mouse immunoglobulins diluted in ration 1:5000. Film was developed in dark room using exposure of 1 minute.

4. Presence of CAR in Isolates of Membrane Proteins from RD-A7 and RD-G7 Cell Lines was Confirmed by Western Blot Analysis Fractions of membrane proteins isolated from RD, RD-A7 and RD-G7 cell lines were analyzed by Western blot analysis in order to check whether CAR was present. FIG. 3 clearly shows that CAR was significantly enriched in fractions of membrane proteins of RD-A7 and especially RD-G7 cell lines, while in fraction of plasma membrane proteins of RD cells CAR is not present. Based on the results obtained, it can be supposed that after coupling magnetic beads with plasma membrane proteins, those magnetic beads with immobilised membrane proteins isolated from RD-G7 would be able to bind more Ad5 viral particles than magnetic beads conjugated with proteins from RD-A7 cells. Binding of Ad5 on to the proteins from RD cells should not occur or be significantly less efficient in comparison with magnetic beads conjugated with proteins from RD-A7 and RD-G7 cells.

5. Adenovirus Type 5 Proteins were Identified with Mass Spectrometry in Eluates of the Magnetic Beads Coupled to the RD-A7 and RD-G7 Membrane Proteins Magnetic beads with immobilised membrane proteins isolated from RD, RD-A7 and RD-G7 cells were incubated with ~$10^{10}$ pp Ad5 according to protocol described in the section 8 of the Methodology part. Eluates of the content bound to the beads with immobilised membrane proteins were sent to the mass spectrometry analysis. Following samples were analysed: Ad5 incubated with magnetic beads coupled to membrane proteins isolated from RD cells (negative control), Ad5 incubated with magnetic beads coupled to membrane proteins isolated from RD-A7 cells and Ad5 incubated with magnetic beads coupled to membrane proteins isolated from RD-G7.

Figure 4:
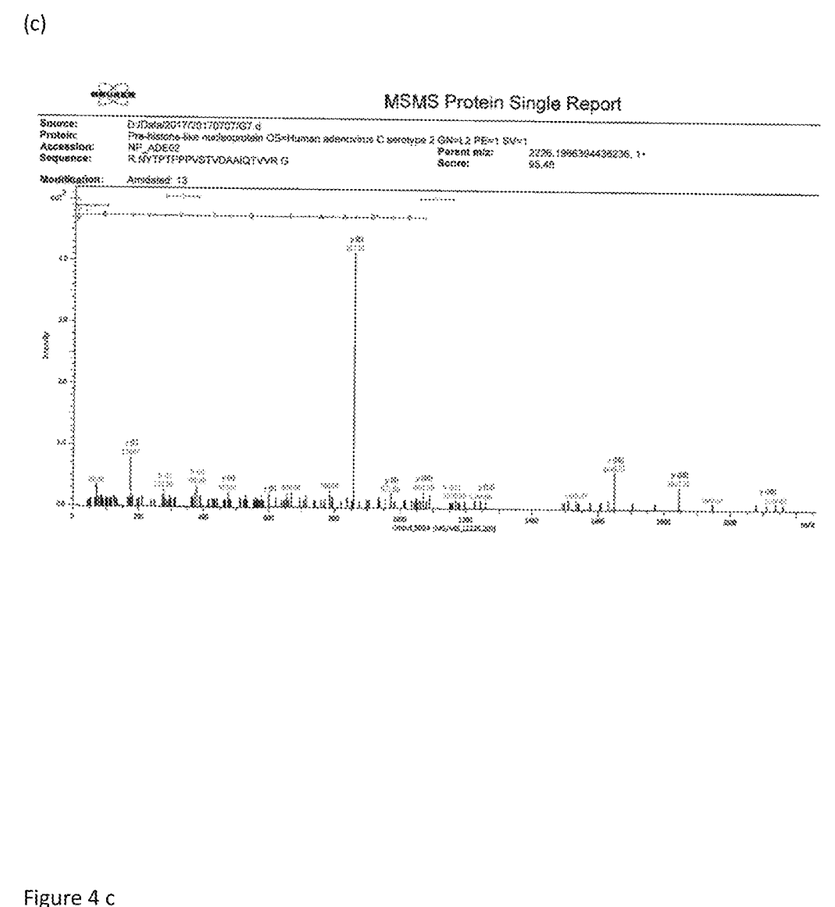
FIG. 4. MSMS spectra of adenovirus type 5 peptides identified in eluates of magnetic beads coupled to membrane proteins (a) RD, (b) RD-A7 and (c) RD-G7 cell lines.
Figure 4A:
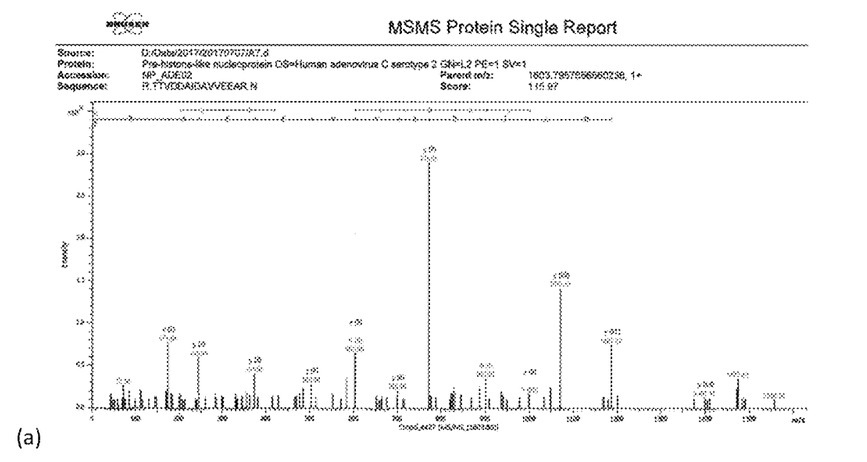
Figure 4B:
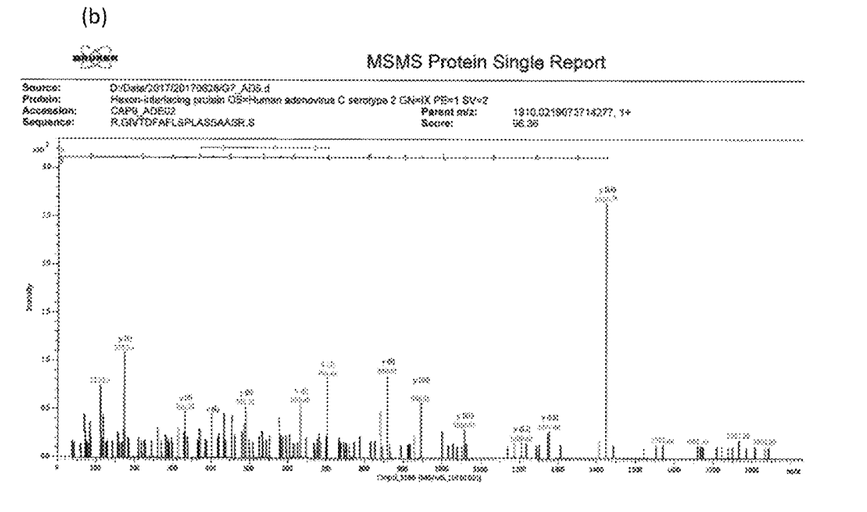

MALDI-TOF/TOF analysis was performed and after search of the SwissProt database it was evident that Ad5 was present in the eluates of the magnetic beads coupled to the the RD-A7 and RD-G7 cell membrane proteins while in the eluates of the beads coupled to the RD cell membrane proteins only BSA and trypsin were detected (present due to the preparation protocol). Identified protein and peptides are shown in table 4 and spectra of identified Ad5 protein is shown in FIG. 4. As expected, more peptides were found in eluates of the beads coupled to the RD-G7 than RD-A7 membrane proteins which contain more CAR.

TABLE 4

Adenovirus type 5 proteins identified in the eluates from magnetic beads coupled to the RD, RD AF and RD G7 cell lmes membrane proteins

| Cell line | Protein Ad5 identified | Accession (SwissProt) | No of peptides | Score | Sequence |
|---|---|---|---|---|---|
| RD | / | / | / | / | / |
| RD A7 | Pre histone like nucleoprotein | NP_ADE02 | 1 | 135.37 | R.TTVDDAIDAVVEFAR.N = SEQ ID No. 1 |
| RD G7 | Hexon interlacing protein | CAP9_ADE02 | 1 | 96.36 | R.GIVTDFAFLSPLASSAASR.S = SEQ ID No. 2 |
|  | Pre histone like nucleoprotein | NP_ADEC02 | 3 | 237.79 | R.APWGAHK.R = SEQ ID No. 3 |

TABLE 4-continued

Adenovirus type 5 proteins identified in the
eluates from magnetic beads coupled to the RD,
RD AF and RD G7 cell lmes membrane proteins

| Cell line | Protein Ad5 identified | Accession (SwissProt) | No of peptides | Score | Sequence |
|---|---|---|---|---|---|
| | | | | | R.TTVDDAIDAVVEEAR.N = SEQ ID No. 1 |
| | | | | | R.NYTPTPPPVSTVDAAIQTVVR.G = SEQ ID No. 4 |

Figure 5:
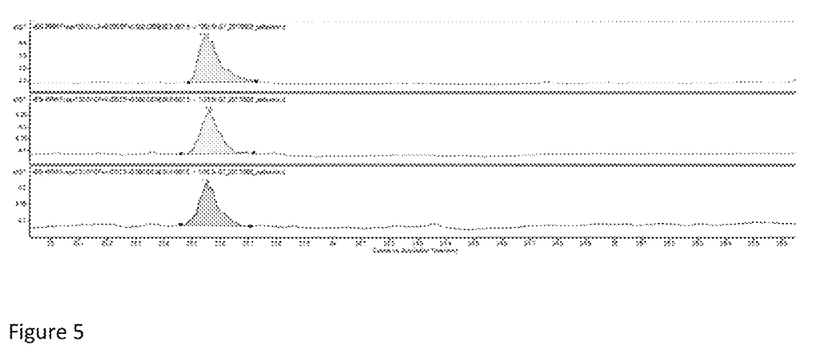
FIG. 5. Representative MRM chromatogram of an identified Ad5 protein.

Additionally, targeted LC-MS analysis was done on eluates from magnetic beads coupled to membrane proteins isolated from RD and RD-G7 cell lines. Identification of the detected peptides was done using in house made data base of Ad5. In LC-MS analysis was evident that Ad5 was present in the eluates of the magnetic beads coupled to membrane proteins isolated from RD-G7 cells while in the eluates of the beads coupled to membrane proteins isolated from RD cells there was no peptides detected. Identified proteins are listed in table 5 and representative MRM chromatogram of one of the identified Ad5 protein is shown in FIG. 5.

TABLE 5

Adenovirus type 5 proteins identified in
targeted LC MS analysis in the eluates
from magnetic beads coupled to membrane
proteins isolated from RD and RD G7 cell
lines.

| Cell line | Protein Ad5 identified | Sequence |
|---|---|---|
| Rd | / | / |
| RD G7 | Pre histone like nucleoprotein | VLAIVNALAENR = SEQ ID No. 5 |
| | | LSAILEAVVPAR = SEQ ID No. 6 |
| | | LLLLLLAPFTDSGSVSR = SEQ ID No. 7 |

---

The invention claimed is:

1. A method for identification of known and unknown viruses in a sample comprising following steps:
   a) collecting and optionally concentrating a sample suspected to contain virus particles;
   b) isolating a total, uncharacterized fraction of membrane proteins of target cells;
   c) immobilizing the membrane proteins isolated in step b) to a carrier, thereby obtaining a carrier with immobilised membrane proteins;
   d) incubating the sample of step a) with the carrier obtained in step c);
   e) separating the carrier of step d) from non-bound material;
   f) detaching the virus particles or parts thereof from the carrier with immobilised membrane proteins;
   g) preparing the virus particles or parts thereof obtained in step f) and determining their peptide sequences using mass spectrometry analysis; and
   h) identifying known virus or viruses by:
      (1) comparing the peptide sequences identified in step g) with databases of known virus peptide sequences; and/or,
      (2) identifying unknown virus or viruses, using sequences identified in step g) by RNA/DNA analysis methods;
   wherein said method for identification enables detection of multiple viruses without requiring prior knowledge of their presence.

2. The method according to claim 1, wherein the sample is a biological sample derived from blood, a body liquid, any tissue sample of a human or animal origin or any swab taken from a human or animal subject.

3. The method according to claim 1, wherein the sample is non-biological sample, a sample taken from soil or swab taken from an object in a human or animal living space, or a sample from an industrial process.

4. The method according to claim 1, wherein target cells are primary cells, any immortalised or tumour cell lines from different origin in human or animal body; or any bacterial strain cells.

5. The method according to claim 1, wherein the carrier suitable for immobilisation of proteins is a magnetic bead or an agarose bead.

6. The method according to claim 1, which is conducted with a diagnostic kit for comprising: a carrier suitable for immobilisation of proteins capable of linking to the membrane proteins of target cells, and a leaflet containing instructions for use.

7. The method according to claim 6, wherein the diagnostic kit further comprises chemicals needed for carrying out steps e)-g) of claim 1.

8. The method according to claim 2, wherein the sample is saliva.

9. The method according to claim 3, wherein the sample is an environmental sample taken from a river, lake, sea, water conduit, water works, or a ventilation system.

10. The method according to claim 3, wherein the sample is taken from a food processing, biotechnological or pharmaceutical process.

* * * * *